(12) United States Patent
Joseph et al.

(10) Patent No.: US 11,972,862 B2
(45) Date of Patent: Apr. 30, 2024

(54) BLOCKCHAIN-BASED TECHNOLOGIES FOR TRACKING PRODUCT LIFECYCLE

(71) Applicant: Mend Medical, LLC, Fort Wayne, IN (US)

(72) Inventors: Benjamin I Joseph, Grabill, IN (US); Seth A Nash, Fort Wayne, IN (US); Bryce A. Isch, Warsaw, IN (US)

(73) Assignee: Mend Medical, LLC, Fort Wayne, IN (US)

( * ) Notice: Subject to any disclaimer, the term of this patent is extended or adjusted under 35 U.S.C. 154(b) by 185 days.

(21) Appl. No.: 17/241,273

(22) Filed: Apr. 27, 2021

(65) Prior Publication Data

US 2021/0343401 A1 Nov. 4, 2021

Related U.S. Application Data

(60) Provisional application No. 63/017,161, filed on Apr. 29, 2020.

(51) Int. Cl.
*G06Q 10/00* (2023.01)
*G06F 16/27* (2019.01)
*G16H 10/20* (2018.01)
*G16H 40/40* (2018.01)

(52) U.S. Cl.
CPC ............ *G16H 40/40* (2018.01); *G06F 16/27* (2019.01); *G16H 10/20* (2018.01)

(58) Field of Classification Search
CPC ......... G16H 40/40; G16H 10/20; G06F 16/27
See application file for complete search history.

(56) References Cited

U.S. PATENT DOCUMENTS

| | | | |
|---|---|---|---|
| 11,176,550 B2* | 11/2021 | Vintila | G06Q 20/3829 |
| 11,269,859 B1* | 3/2022 | Luedtke | G06F 16/245 |
| 11,416,944 B1* | 8/2022 | Floyd | G06Q 20/223 |
| 11,507,562 B1* | 11/2022 | Luedtke | G06F 16/254 |
| 11,605,124 B2* | 3/2023 | Cella | G06N 3/045 |
| 2011/0054936 A1* | 3/2011 | Cowan | G16H 40/67 |
| | | | 705/2 |
| 2017/0246465 A1* | 8/2017 | Ben-Haim | A61N 1/36007 |
| 2020/0000952 A1* | 1/2020 | Dang | A61L 2/07 |
| 2022/0059218 A1* | 2/2022 | Fischer | G16H 40/40 |

\* cited by examiner

*Primary Examiner* — Rajesh Khattar
(74) *Attorney, Agent, or Firm* — Barnes & Thornburg LLP

(57) ABSTRACT

Blockchain-based technologies to facilitate traceability of products through their lifecycle, including design, development, manufacturing, supply chain, and use. The system provides transparent, secure traceability through product lifecycle, drawing insights from collected data and post-market activities. For example, the system could receive tracking data from a plurality of tracking sources along a product's lifecycle and generate one or more blocks in a blockchain to capture the tracking data from the plurality of tracking sources along the product's lifecycle in one or more distributed ledgers.

19 Claims, 4 Drawing Sheets

BLOCKCHAIN-BASED TECHNOLOGIES FOR TRACKING PRODUCT LIFECYCLE

RELATED APPLICATIONS

This application claims the benefit of U.S. Provisional App. No. 63/017,161 for "Blockchain-Based Technologies for Tracking Product Lifecycle" filed Apr. 29, 2020, which is hereby incorporated by reference in its entirety.

TECHNICAL FIELD

This disclosure relates generally to a blockchain-based technology for providing traceability of products through their lifecycle from design to post-market activities; in particular, this disclosure relates to a system that provides visibility, tracking, and traceability to the product's design, procurement, manufacture, supply chain, and post-market activities.

BACKGROUND

A product goes through several phases to get to users, including design, procurement, manufacture, and supply chain. For example, in the medical, aviation, defense, and pharmaceutical industries, there are challenges tracing a product as it goes through these phases. One challenge is the disparate systems used by parties in each phase. For example, there could be separate design and manufacturing systems. Even in a single company, there may be complex supply chains with multiple vendors, and the data may not reside completely within that company.

For example in the medical device industry, nearly every major market requires implementation and maintenance of a Quality Management System (QMS) as a condition of product registration and commercialization. Device manufacturers in Europe, Canada, Australia, and other countries follow the ISO 13485 standard, while U.S. companies comply with the Quality System Regulation (QSR) outlined by the FDA. Regardless of the standard followed, medical device companies implement a harmonized QMS which integrates the standard requirements for products in which they commercialize.

The link between a product and the associated QMS is critical to understanding the method by which regulatory bodies monitor compliance. In Europe, the requirement for product distribution is to obtain a CE mark. The most common way to prove compliance is by demonstrating applicable QMS and technical documentation meet the requirements of ISO 13485. Certification for meeting these requirements is typically done through third-party organizations known as Notified Bodies (NB).

Within the U.S., FDA requires compliance with 21 CFR Part 820 at the time of registration. FDA expects compliance with the QSR but does not require proof when registering a device. Enforcement is accomplished through random inspections in which FDA audit inspectors may arrive at a device manufacturer's door at any time. For this reason, documentation of QMS processes, events, workflows are critically important.

While QMS documentation should be viewed as a favorable means to prove compliance in the event of an audit, often the very notion can create angst within a company. Many times, QMS processes and procedures are overly burdensome and at times inadequate with respect to the purpose of proving compliance.

A QMS is comprised of the core set of business policies, procedures, forms, and work instructions, along with their sequence, interactions, and resources required to conduct business within a medical device company. Quality records provide objective evidence in the form of documentation which demonstrate the QMS is being executed, followed, and identified requirements are being met. Quality systems and subsystems are defined in FDA regulation 21 CFR part 820. A QMS incorporates any number of subsystems, such as material controls, facility & equipment controls, medical device reporting, reports of corrections and removals, medical device tracking, corrective & preventative actions, design controls, production & process controls, and sterilization process controls, which are subject to compliance requirements and audit capability.

From a regulatory standpoint, the QMS is the pulse of the business and ensures the safety and effectiveness of medical devices on the market. The expectation is that the management team sits at the center of the quality system and provides oversight to ensure the safety and effectiveness of the devices being manufactured. Any number of the above subsystems such as Corrective and Preventative Action (CAPA), Medical Device Reporting, Production and Process Controls and others identified with the QMS may be audited and are expected to be found in compliance with regulation standards.

Of all the QMS subsystems identified, the Design Controls system is the most complex from an audit and control perspective. Within the design controls system sits the Design History File (DHF) containing the references and records necessary to demonstrate the device design was developed in accordance with the approved design plan and requirements of 21 CFR part 820. Each medical device manufacturer is required to establish and maintain a DHF for every device. During the development of a medical device, there are several events, such as defining user needs, design input, design process, design output, design verification, design validation, and device reviews.

Regulators expect device makers to implement controls for production and processes to ensure device traceability and integrity. However, product delivery to the patient is not always linear and may be repeated any number of times before device usage. More recent regulations have added additional complexity to the tracking of medical devices. The addition of unique device identification (UDI) has recently been established to adequately identify medical devices from manufacturing through distribution to patient use. When fully implemented, the label of most devices will include a UDI in human and machine readable form, which will improve patient safety and modernize post-market surveillance. However, identifying elements, such as device history records, design control or UDI/serial number traceability of the design, supply chain, instrument usage, drawing insights from collected data, and post market activity can be a time-consuming and burdensome process.

SUMMARY

According to one aspect, this disclosure provides a computing system to facilitate integration and tracking of a medical device lifecycle. The computing system comprises one or more distributed ledgers implemented on the computing system to establish a blockchain that secures data relating to a medical device lifecycle, a processor, and a memory coupled to the processor and having stored therein a plurality of instructions that, when executed, cause the server to: receive tracking data from a plurality of tracking sources along the medical device lifecycle; and generate one or more blocks in the blockchain to capture the tracking data from the plurality of tracking sources along the medical device lifecycle in the one or more distributed ledgers.

According to another aspect, this disclosure provides a non-transitory computer-readable medium that stores computer executable instructions for causing one or more processors of a server to facilitate integration and tracking of a medical device lifecycle comprising: receive tracking data from a plurality of tracking sources along a medical device lifecycle; and generate one or more blocks in a blockchain to capture the tracking data from the plurality of tracking sources along the medical device lifecycle in one or more distributed ledgers.

According to a further aspect, this disclosure provides method comprising: receiving tracking data from a plurality of tracking sources along a medical device lifecycle; and generating one or more blocks in a blockchain to capture the tracking data from the plurality of tracking sources along the medical device lifecycle in one or more distributed ledgers.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
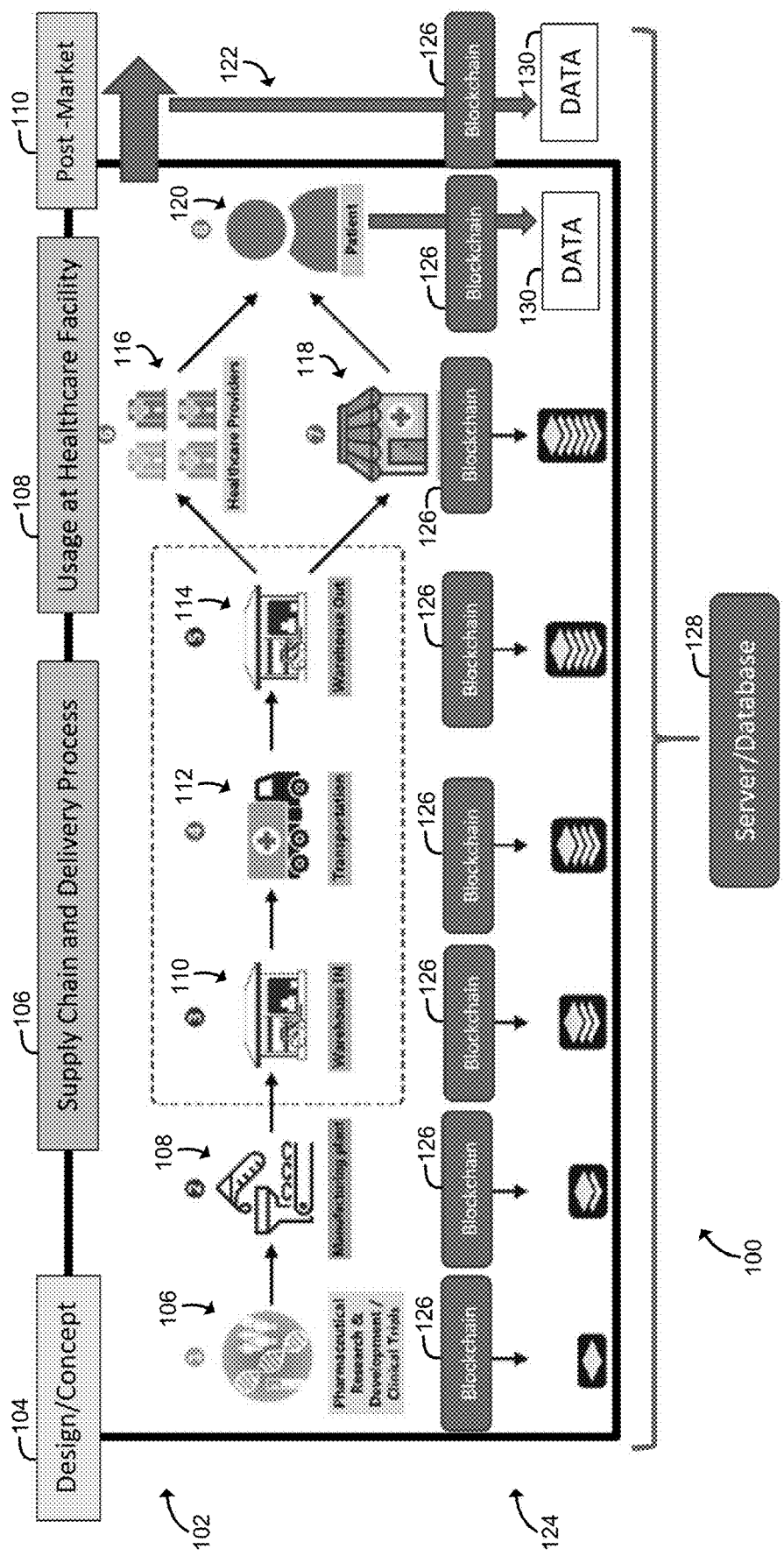
FIG. 1 is a simplified block diagram of at least one embodiment of a blockchain-based system for tracking a product lifecycle.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a blockchain-based system 100 that provides visibility, tracking, and traceability to a product's design, procurement, manufacture, supply chain, and post-market activities on an individualized product level. Although the system 100 will be discussed primarily with respect to medical and pharmaceutical devices for purposes of example, other types of products could be traced with the system, including but not limited to products in the aviation, defense, and/or automotive industries. Embodiments of the system 100 could be used with any product type and any industry in which the product is capable of being individually identified in some way, whether in a human-readable or machine-readable manner.

The system 100 facilitates identification, traceability, and integrity of product lifecycles for individual products. In the example shown, the system 100 includes a plurality of lifecycle phases 102 each of which generate events related to an individual product as that product goes through the phases 102. For example, there could be a plurality of computing systems that generate events relating to design 106, manufacturing 108, warehouse inventory 110, transportation 112, warehouse shipments 114, product usage by healthcare providers 116, product usage by healthcare facilities 118, patient feedback 120, and/or post-market activities 122. Each of these systems are sources of tracking data 106, 108, 110, 112, 114, 116, 118, 120, 122 regarding the individual product and are captured through a distributed ledger 124 with one or more blockchains 126 on one or more servers 128. For example, in the design/concept phase 106, any events related to the design and associated documentation from the product's design history file (DHF) could be tied to an individual product that is captured within the distributed ledger 124. Although the sources of tracking data 106, 108, 110, 112, 114, 116, 118, 120, 122 are shown for purposes of example, other potential sources of tracking data could be provided depending on the circumstances.

Although a single server 128 is shown in FIG. 1 for purposes of example, one skilled in the art should appreciate that more than one server 128 could be used depending on the circumstances. For example, the server 128 could be a cloud-based platform with a plurality of servers accessible through a communication network. The server 128 may be embodied as any type of computation or computer device capable of performing the functions described herein, including, without limitation, a computer, a server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. Additionally or alternatively, the server 128 may be embodied as a one or more compute sleds, memory sleds, or other racks, sleds, computing chassis, or other components of a physically disaggregated computing device. Depending on the circumstances, the server 128 could include a processor, an input/output subsystem, a memory, a data storage device, and/or other components and devices commonly found in a server or similar computing device. Of course, the server 128 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory, or portions thereof, may be incorporated in the processor in some embodiments. The server 128 includes a communication subsystem, which may be embodied as any communication circuit, device, or collection thereof, capable of enabling communications between the server 128 and sources of tracking data (and other devices) over a computer network. For example, the communication subsystem may be embodied as or otherwise include a network interface controller (NIC) or other network controller for sending and/or receiving network data with remote devices. The NIC may be embodied as any network interface card, network adapter, host fabric interface, network coprocessor, or other component that connects the server 128 to the network. The communication subsystem may be configured to use any one or more communication technology (e.g., wired or wireless communications) and associated protocols (e.g., Ethernet, InfiniBand®, Bluetooth®, Wi-Fi®, WiMAX, 3G, 4G LTE, etc.) to effect such communication.

As shown, the system 100 includes one or more interfaces or data views 130 though which users can access the distributed ledger 124, which provides a distributed, independently verifiable record of an individual product that could potentially be accessed by the patient, a regulator, a third party body for post-market analysis, or others. For example, the server 128 may include a web-based interface or portal through which users of the remote computing devices can interact with features of the server 128 using a browser, such as Chrome™ by Google, Inc. of Mountain View, California Embodiments are also contemplated in which the server 128 could establish a cloud-based platform (e.g., SaaS platform) through which remote computing devices may send messages using an app running on the Android™ operating system by Google, Inc. of Mountain View, California and/or an app running on the iOS™ operating system by Apple Inc. of Cupertino, California on which software has been installed to perform one or more actions according to an embodiment of the present disclosure. For example, the computing devices 104 may have an app installed that allows a user to perform one or more actions described herein, such as data views 130. Although the system 100 is described as being a cloud-based platform accessible by the remote computing devices, in some embodiments one or more features of the server 128 could be performed locally on the remote computing devices depending on the circumstances.

There are several technical advantages of the system 100. For example, the system 100 securely integrates tracking data from a plurality of tracking sources, such as events from disparate systems regarding a product's design, procurement, manufacture, supply chain, sale, usage, and post-market activities, along a product's lifecycle in a manner that individual products are identified in a unique way. The term "product lifecycle" is broadly intended to encompass each phase of the product from design and development, procurement, manufacture, supply chain, sale, usage, and post-market activities. Instead of manually attempting to cobble together data from disparate systems to comply with regulatory requirements, which is time consuming and potentially error-prone, the system 100 integrates documentation of the product's lifecycle in a secure, but transparent manner through a distributed ledger system. The distributed ledger transparently and securely tracks each "event" in the product's lifecycle (e.g., a design change, a manufacturing deviation, an inventory move transfer, a sale, post-sale event, etc.), by generating blocks in the blockchain to capture these events, regardless of which system along the lifecycle creates an event. In some cases, for example, a clinical study on a medical device or a service call or inspection on a piece of equipment could be uniquely identified in the individual product's device history via the distributed ledger 124. The tracking data could be accessed for a variety of purposes, such as to ensure compliance with regulatory authorities, clinical studies, patient record regarding his/her device, etc. Another technical advantage of the system 100 is a secure, patient record for their individual device. As discussed above, the system 100 may include one or more data view, such as a patient view in which every event along the lifecycle of the patient's device could be recorded.

Figure 2:
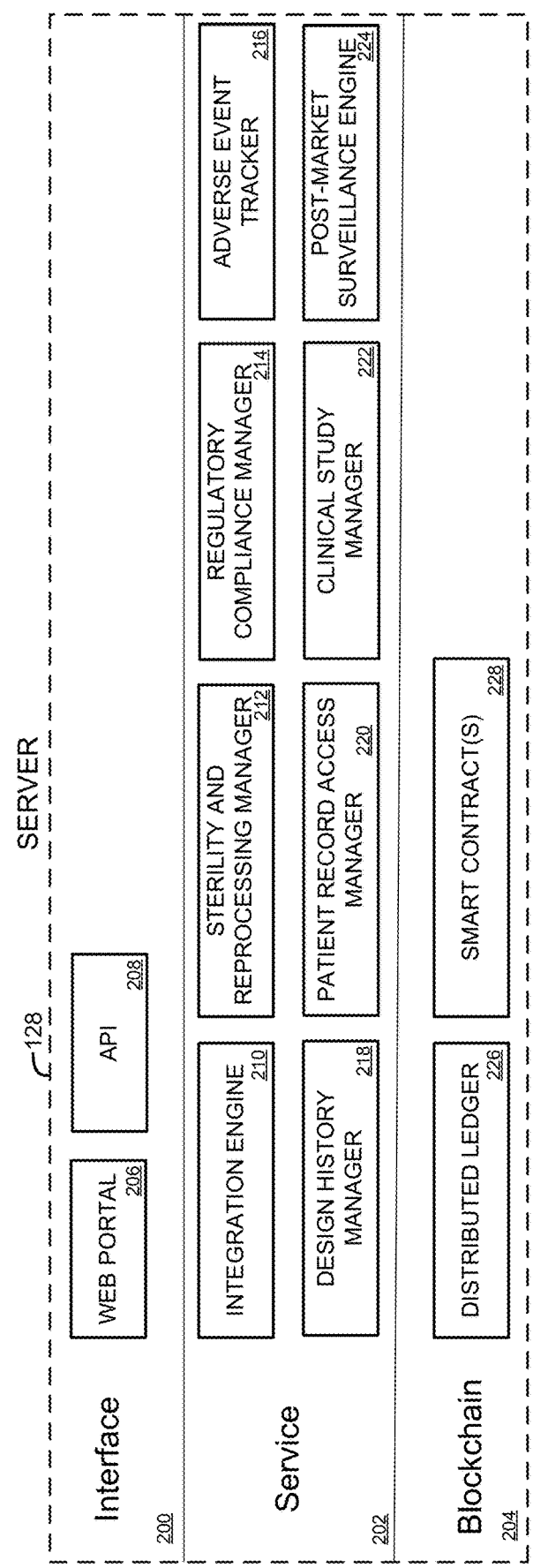
FIG. 2 is a simplified block diagram of at least one embodiment of various environments of the server of FIG. 1.

Referring now to FIG. 2, in an illustrative embodiment, the server 128 establishes an environment 200 during operation for providing visibility, tracking, and traceability to a product's design, procurement, manufacture, supply chain, and post-market activities on an individualized product level. In the embodiment shown, the illustrative environment 200 includes an interface layer 200, a service layer 202, and a blockchain layer 204. Although these three layers are shown for purposes of example, one skilled in the art should appreciate that more or less layers could be provided depending on the circumstances.

As shown, the interface layer 200 includes a web portal 206 and an application programming interface (API) 208. The service layer 202 includes an integration engine 210, a sterility and reprocessing manager 212, a regulatory compliance manager 214, an adverse event tracker 216, a design history manager 218, a patient record access manager 220, a clinical study manager 222, and a post-market surveillance engine 224. In the embodiment shown, the blockchain layer 204 includes a distributed ledger 226 and one or more smart contracts 228. As shown, the various components of the environment 200 may be embodied as hardware, firmware, software, or a combination thereof. As such, in some embodiments, one or more of the components of the environment 200 may be embodied as circuitry or collection of electrical devices (e.g., integration engine circuitry 210, a sterility and reprocessing manager circuitry 212, a regulatory compliance manager circuitry 214, an adverse event tracker circuitry 216, a design history manager circuitry 218, a patient record access manager circuitry 220, a clinical study manager circuitry 222, and a post-market surveillance engine circuitry 224, distributed ledger circuitry 226 and smart contract circuitry 228). In the illustrative embodiment, the integration engine circuitry 210, a sterility and reprocessing manager circuitry 212, a regulatory compliance manager circuitry 214, an adverse event tracker circuitry 216, a design history manager circuitry 218, a patient record access manager circuitry 220, a clinical study manager circuitry 222, and a post-market surveillance engine circuitry 224, distributed ledger circuitry 226 and smart contract circuitry 228 are embodied as hardware, firmware, or other resources of the server 128. Additionally or alternatively, in some embodiments, those components may be embodied as hardware, firmware, or other resources of the computing device 104. Additionally, in some embodiments, one or more of the illustrative components may form a portion of another component and/or one or more of the illustrative components may be independent of one another.

The integration engine 210 is configured to receive data from the plurality of tracking data sources 106, 108, 110, 112, 114, 116, 118, 120, 122 regarding an individual product and generate one or more blocks in the distributed ledger 226 that links the tracking data to a unique product identifier (UPI) or some other identifier that uniquely identifies an individual product. The unique identifier could be human and/or machine readable and may be engraved, embedded, labelled, printed, or otherwise associated with the individual product. As discussed herein, each time there is an event regarding the individual product that generates tracking data, the integration engine 210 receives the tracking data and generates one or more blocks in the distributed ledger 226 that links the tracking data to the individual product based on the unique identifier. Whenever there is an event regarding the individual product in any of the phases 102, 106, 108, 110 of the product's lifecycle, whether design data, manufacturing data, supply chain data, usage or sales data, or post-market data, the tracking data is received by the integration engine via the web portal 206 or the API 208 (or other interface 200). For example, the blockchain record could be updated by the integration engine 210 with each inventory transfer, accounting not only for location but creating a clear chain of custody for sensitive products like medical devices or could be used in non-medical device industries for products like weapons, aviation, military or other regulated products. The integration engine 210 is configured to generate one or more blocks in the blockchain 126 based on the tracking data received via the web portal 206 and the API 208. These blocks include the unique identifier for the individual product.

Figure 3:
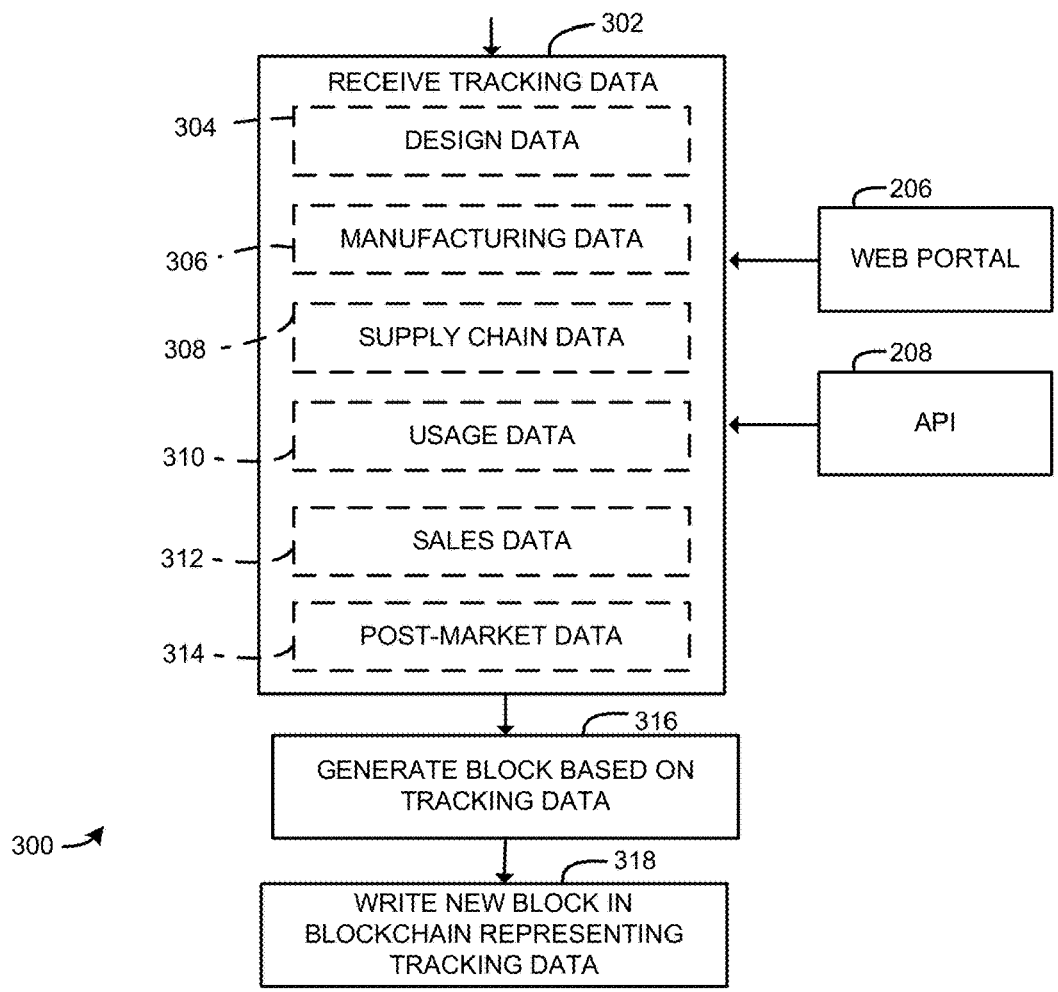
FIG. 3 is a simplified flow diagram of at least one embodiment of a method for generating one or more blocks in a blockchain regarding tracking data associated with an individual device.

FIG. 3 illustrates a method 300 for generating blocks in a distributed ledger 226 based on tracking data that may be executed by the server 128. It should be appreciated that, in some embodiments, the operations of the method 300 may be performed by one or more components of the environment 200 of the server 128 as shown in FIG. 2, such as the integration engine 210. Also, it should be appreciated that the order of steps for the method 300 shown in FIG. 3 are for purposes of example, and could be in a different order; likewise, depending on the circumstances, some steps shown in the method 300 may be optional, or may not always be performed by the integration engine 210. As illustrated, the method 300 begins in block 302 in which tracking data is received, such as from the web portal 206 and/or the API 208. The tracking data could be from a plurality of data sources along the product lifecycle, such as design data 304, manufacturing data 306, supply chain data 308, usage data 310, sales data 312, and/or post-market data 314. As discussed herein, any event relating to the individual product throughout the product lifecycle could trigger a communication from systems along the product lifecycle with the web portal 206 and/or API 208 to send message(s) with tracking data regarding the event. In some embodiments, the integration engine 210 could be configured to register systems that may have tracking data along the product's lifecycle with the system 100. For example, the integration engine 210 could assign a tracking source identifier to systems registered with the system 100. In some cases, these messages could include the unique identifier for the individual product, such as the UDI. In some cases, the message may include a unique identifier associated with the tracking source, such as the tracking source identifier. Next, the method 300 advances to block 316 in which a block for the blockchain is generated based on the tracking data. The method 300 proceeds to block 318 in which the block based on the received tracking data is written to the blockchain. The integration engine 210 provides the ability to capture tracking documentation to the distributed ledger 226 and creates a consolidated approach to tracking documentation changes, change requests, or other associated change points which occur through the product's lifecycle, such as within the design control process, and allows a product history to be created in a cloud environment by the server 128.

Figure 4:
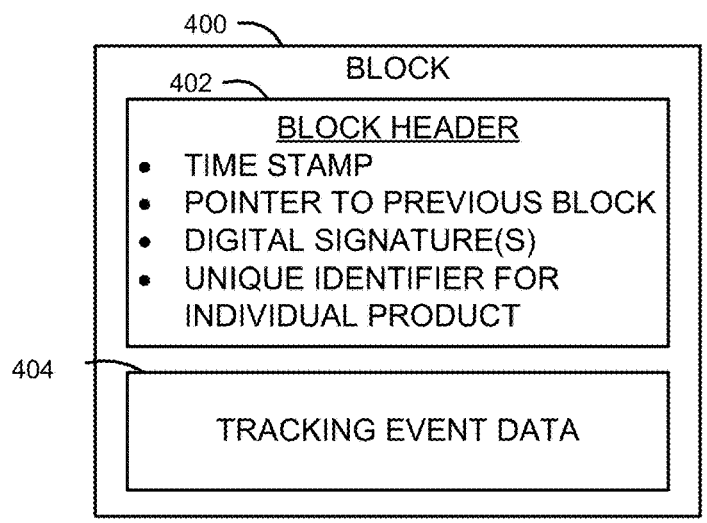
FIG. 4 is a simplified block diagram of at least one embodiment of a block in the blockchain created upon receiving tracking data.

FIG. 4 illustrates an example block that could be added to the distributed ledger 226 by the integration engine 210. In this example, the new block 400 includes a block header 402 and tracking event data 404. As shown, the block header 402 includes information that provides a traceability for the individual product. For example, the block header 402 could include a time stamp when the block 400 is created. If there are existing blocks in the blockchain (i.e., the new block is not the genesis block), the block header 402 could include a pointer to the previous block in the blockchain. Depending on the circumstances, the block header 402 could include a digital signature, such as the organization or person from which the tracking data originated. Instead, or in addition to the digital signature, the unique identifier could be included in the block header 402 and/or tracking event data 404. For example, the message to the API 208 could include a digital signature of the organization providing tracking data and/or a digital signature of the system 100 to validate the block. This provides a technical advantage of transparently tracking the product based on a unique identifier for the device. The block 400 may also include a payload with transactional information about the tracking event.

Referring again to FIG. 2, sterility and reprocessing manager 212 is configured to track sterility cycle information and reprocessing of medical devices. For example, the sterility and reprocessing manager 212 could identify specific sterility cycle information and reprocessing of medical devices on an individual product level. By way of example, the sterility and reprocessing manager 212 could pull together critical parameters like sterilization cycle time, for example, based on a unique identifier of the medical device and report this information (and other sterilization/reprocessing information) through the web portal 206 and/or API 208. This provides a technical benefit of determining whether potential exposure of non-sterile medical devices have occurred since leaving an OEM manufacturing facility.

The regulatory compliance manager 214 is configured to report compliance information based on blocks in the distributed ledger 226. For example, the regulatory compliance manager 214 may include one or more business rules specific to compliance with one or more regulations. The regulatory compliance manager 214 may query the distributed ledger as a function of the product identifier based on the one or more business rules. For example, the web portal 206 may include a regulatory compliance interface that allows a user to select one or more compliance reports. The regulatory compliance manager 214 may generate compliance reports automatically by querying the distribute ledger 226 for the information that needs to be gathered to the selected report based on the business rules. Due to the blocks in the distributed ledger 226, there is a secure audit trail for these compliance reports.

The adverse event tracker 216 is configured to determine individual products subject to an adverse event. For example, the adverse event data could be received from any of the plurality of tracking data sources by the integration engine 210 and one or more blocks added to the distribute ledger 226 linked to the individual product identifier. In this manner, customer complaints, service issues or other problems could more accurately be tracked among disparate systems and the blockchain could ensure the integrity of the record. In the event of recalls or field actions, manufacturers and regulators could locate and identify affected customers and products based on the distributed ledger 226.

The design history manager 218 is configured to report a design history file regarding the individual product as a function of the unique product identifier through the web portal 206 or API based on one or more blocks in the distributed ledger 226. This provides transparency from the distributed ledger 226 through the product's lifecycle to track documentation changes, change requests and associated change points. The allows a medical device manufacturer to create transparency from concept through the lifecycle of each individual product by capturing the conception of the design and all associated documentation from the design history file (DHF) tied to an individual product in the blockchain. By providing the ability to track documentation from a distributed ledger, this creates a consolidated approach to tracking documentation changes, change requests, or other associated change points which occur within the design control process and allows a product history to be created in a cloud environment.

The patient record access manager 220 is configured to provide patient access to review device information and post-market activities provided by OEMs. For example, the patient may access information from blocks in the distributed ledger 226 regarding their specific, individual device through the web portal 206 and/or API 208. This enhances safety by creating a distributed, independently verifiable, record that could potentially be owned/accessed by the patient.

The clinical study manager 222 is configured to enroll an individual device in a clinical study and links transactions about the device in the study. For example, a clinical study identifier could be associated with the unique product identifier for the device in one or more blocks in the distributed ledger 226. A researcher (or other user) could access blocks in the blockchain associated with the clinical study through the web portal 206 or API 208. By way of example, an implanted medical device enrolled in a clinical study could be linked via the blockchain for both post-market surveillance requirements and novel clinical study methods not available without device-specific tracking. Unlike this disclosure, current standard of medical device implant production lot control limit transparency to "Iot" levels and does not provide individual insight to specific devices affected.

The post-market surveillance engine 224 is configured to allow healthcare providers to access patient information gathered as part of post-market surveillance activities. Using blockchain technology in the form of the distributed ledger 226 would provide access to patient outcome information in an open reporting format without the risk of violating patient privacy laws. Additionally, post-market clinical data could be accessed by regulatory bodies for clinical study, device useful life, usability, or human factor purposes.

Figure 5:
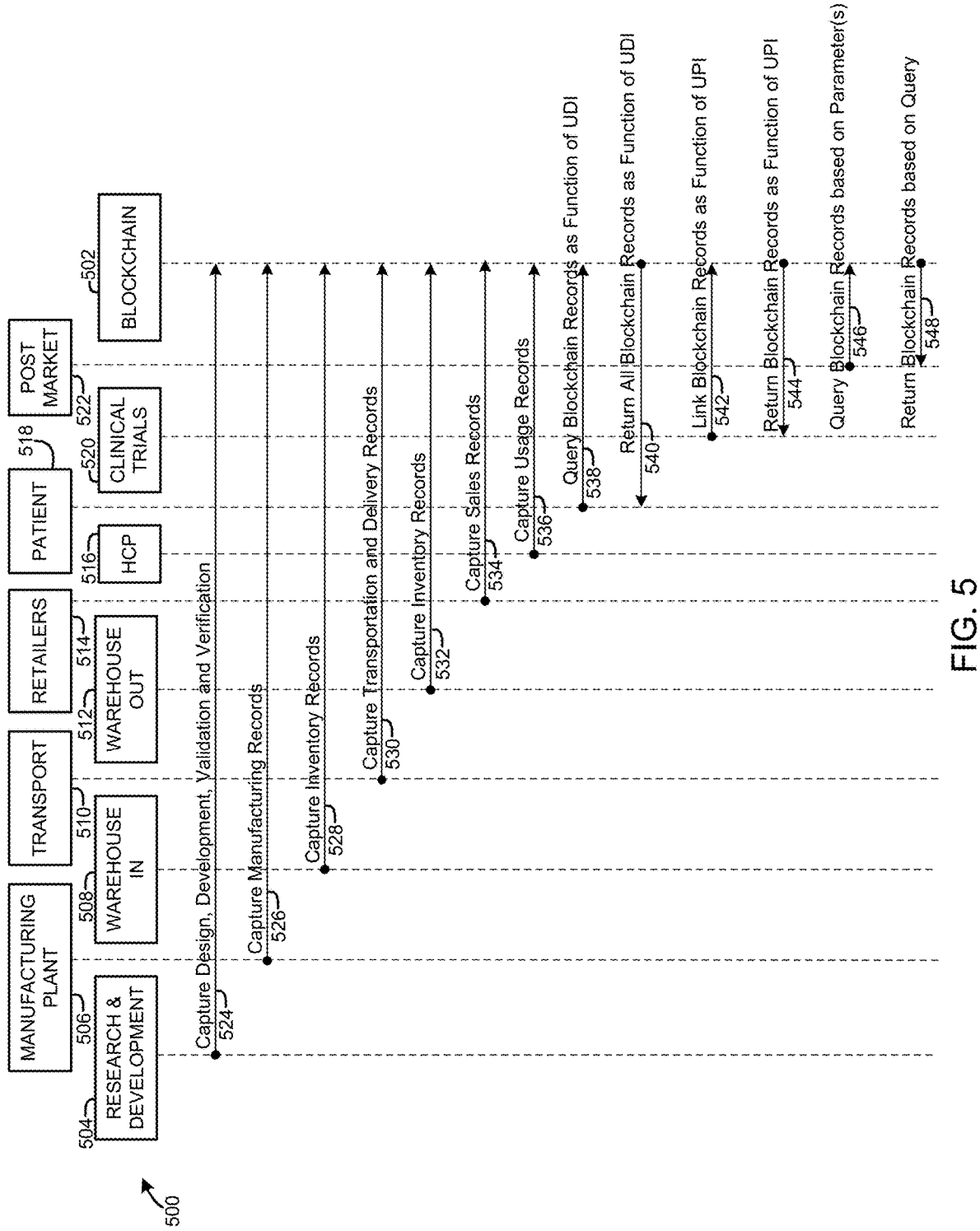
FIG. 5 is a simplified flow diagram of at least one embodiment illustrating messaging flow of the system shown in FIG. 1.

FIG. 5 illustrates an embodiment of the system 100 showing message flow with a plurality of computing devices 500, which each interact with a blockchain 502 to capture tracking data and/or report information about an individual device linked to the blockchain 502. In the example shown, there is a research and development computing device 504, a manufacturing plant computing device 506, a warehouse in computing device 508, a transport computing device 510, a warehouse out computing device 512, a retailers computing device 514, a healthcare provider computing device 516, patient computing device 518, a clinical trials computing device 520, and a post-market computing device 522. These plurality of computing devices 500 are shown merely for purposes of example and additional computing devices could be provided to supply tracking data and/or receive reporting data from the blockchain 502 depending on the circumstances. Although a single computing device is shown at various phases in the product's lifecycle for purposes of example, there could be a plurality of computing devices at one or more of the phases. By way of example, the manufacturing plant computing device 506 could represent a plurality of computing devices along the manufacturing process that each generate data regarding the product and capture the tracking data to the blockchain 502.

In the example shown, the research and development computing device 504 sends one or more messages 524 with tracking data regarding design, development, validation and/or verification of the device to the system 100, such as programmatically via the API 208, and the integration engine 220 captures the tracking data in the blockchain 502 based on an identifier that uniquely identifies the individual product. During the manufacture of the device, the manufacturing plant computing device 506 sends one or more messages 526 with tracking data regarding manufacture of the device to the system 100, such as via the API 208, and the integration engine 210 captures the tracking data regarding manufacturing in the blockchain 502 based on an identifier that uniquely identifies the individual product. During the supply chain phase, the warehouse in computing device 508, transport computing device 510, and warehouse out computing device 512 send one or more messages 528, 530, 532 with tracking data regarding logistics information about the device in the supply chain to the system 100, such as via the API 208, and the integration engine 210 captures the tracking data regarding the supply chain in the blockchain 502 based on an identifier that uniquely identifies the individual product. In this example, the retailers computing device 514 sends one or more messages 534 with tracking data regarding sales information about the device to the system 100, such as via the API 208, and the integration engine 210 captures the tracking data regarding the sale in the blockchain 502 based on an identifier that uniquely identifies the individual product. The healthcare provider computing device 516, in the example shown, sends one or more messages 536 regarding usage of the device, such as installation time in the operating room, to the system 100, such as via the API 208, and the integration engine 210 captures the tracking data regarding the device usage in the blockchain 502 based on an identifier that uniquely identifies the individual product.

In the example shown, the patient computing device 518 sends one or more messages 538 to the system 100 to query about his/her device as a function of a unique device identifier. As shown, the system 100 returns one or more messages 540 to the patient computing device 518 with the blockchain records matching the query, such as using the patient record access manager 220. As shown, the clinical trials computing device 520 sends one or more messages 542 to the system 100 that include a clinical study identifier to link blockchain records with the clinical study as a function of the unique device identifier. Once the individual device is linked with a clinical study, the system 100 can send one or more message 544 to return blockchain data regarding the clinical study, such as using the clinical study manager 222. In this example, the post-market computing device 522 sends one or more messages 546 to query blockchain records based on one or more parameters of the individual device as a function of the unique identifier associated with the device. The system 100 returns one or more messages 548 with the blockchain records having parameters matching the query.

EXAMPLES

Illustrative examples of the technologies disclosed herein are provided below. An embodiment of the technologies may include any one or more, and any combination of, the examples described below.

Example 1 includes a computing system to facilitate integration and tracking of a medical device lifecycle. The computing system comprising: a processor; a memory coupled to the processor and having stored therein a plurality of instructions that, when executed, cause the server to: one or more distributed ledgers implemented on the computing system to establish a blockchain that secures data relating to a medical device lifecycle; receive tracking data from a plurality of tracking sources along the medical device lifecycle; and generate one or more blocks in the blockchain to capture the tracking data from the plurality of tracking sources along the medical device lifecycle in the one or more distributed ledgers.

Example 2 includes the subject matter of Example 1, and further comprising one or more instructions to generate one or more blocks in the blockchain responsive to receiving tracking data from one or more of the plurality of tracking sources along the medical device lifecycle.

Example 3 includes the subject matter of Examples 1-2, and wherein: to generate one or more blocks in the blockchain as a function of one or more parameters of a respective tracking source of the plurality of tracking sources.

Example 4 includes the subject matter of Examples 1-3, and wherein: to generate one or more blocks in the blockchain comprises triggering generating the one or more blocks responsive to receiving tracking data from one or more of the plurality of tracking sources along the medical device lifecycle.

Example 5 includes the subject matter of Examples 1-4, and wherein: the plurality of tracking sources comprises tracking data representing one or more of design, manufacturing, or supply chain events regarding an individual medical device.

Example 6 includes the subject matter of Examples 1-5, and wherein: the individual medical device comprises one or more of an imbedded medical device or a pharmaceutical product.

Example 7 includes the subject matter of Examples 1-6, and further comprising: generating one or more blocks in the blockchain that link tracking data representing one or more of design, manufacturing, or supply chain events regarding the individual medical device with a unique identifier for the individual medical device.

Example 8 includes the subject matter of Examples 1-7, and wherein: to generate comprises generating one or more blocks in the blockchain that link tracking data representing healthcare usage events regarding the individual medical device with the unique identifier for the individual medical device.

Example 9 includes the subject matter of Examples 1-8, and wherein: to generate comprises generating one or more blocks in the blockchain that link tracking data representing one or more of reprocessing or sterility cycle information regarding the individual medical device with the unique identifier for the individual medical device.

Example 10 includes the subject matter of Examples 1-9, and further comprising one or more instructions to enroll the individual medical device in a clinical study, wherein to generate comprises generating one or more blocks in the blockchain that link tracking data representing one or more of reprocessing or sterility cycle information regarding the individual medical device with the unique identifier for the clinical study.

Example 11 includes the subject matter of Examples 1-10, and wherein: to generate comprises generating one or more blocks in the blockchain that link adverse event data representing one or more of a recall or a field action event regarding the individual medical device with the unique identifier for the individual medical device.

Example 12 includes the subject matter of Examples 1-11, and further comprising one or more instructions to generate an alert responsive to one or more blocks in the blockchain including adverse event data.

Example 13 includes the subject matter of Examples 1-12, and further comprising selectively providing access to one or more users to the one or more blocks in the blockchain.

Example 14 includes the subject matter of Examples 1-13, and further comprising one or more instructions to present one or more blocks in the blockchain as a function of the unique identifier for the individual medical device.

Example 15 includes a non-transitory computer-readable medium that stores computer executable instructions for causing one or more processors of a server to facilitate integration and tracking of a medical device lifecycle comprising: receive tracking data from a plurality of tracking sources along a medical device lifecycle; and generate one or more blocks in a blockchain to capture the tracking data from the plurality of tracking sources along the medical device lifecycle in one or more distributed ledgers.

Example 16 includes the subject matter of Example 15, and further comprising one or more instructions to automate generation of one or more blocks in the blockchain responsive to receiving tracking data from one or more of the plurality of tracking sources along the medical device lifecycle.

Example 17 includes the subject matter of Examples 15-16, and wherein: the one or more automated routines are to generate one or more blocks in the blockchain as a function of a respective tracking source of the plurality of tracking sources.

Example 18 includes the subject matter of Examples 15-17, and wherein: the one or more automated routines are triggered responsive to receiving tracking data from one or more of the plurality of tracking sources along the medical device lifecycle.

Example 19 includes the subject matter of Examples 15-18, and wherein: to generate comprises generating the one or more blocks in the blockchain by including uniquely identify an individual medical device.

Example 20 includes the subject matter of Examples 15-19, and wherein: the plurality of tracking sources comprises tracking data representing one or more of design, manufacturing, and supply chain events regarding the individual medical device.

Example 21 includes the subject matter of Examples 15-20, and wherein: to generate comprises generating one or more blocks in the blockchain that link tracking data representing one or more of design, manufacturing, and supply chain events regarding the individual medical device with a unique identifier for the individual medical device.

Example 22 includes the subject matter of Examples 15-21, and wherein: to generate comprises generating one or more blocks in the blockchain that link tracking data representing healthcare usage events regarding the individual medical device with the unique identifier for the individual medical device.

Example 23 includes the subject matter of Examples 15-22, and wherein: to generate comprises generating one or more blocks in the blockchain that link tracking data representing one or more of reprocessing or sterility cycle information regarding the individual medical device with the unique identifier for the individual medical device.

Example 24 includes the subject matter of Examples 15-23, and further comprising one or more instructions to enroll the individual medical device in a clinical study, wherein to generate comprises generating one or more blocks in the blockchain that link tracking data representing one or more of reprocessing or sterility cycle information regarding the individual medical device with the unique identifier for the clinical study.

Example 25 includes the subject matter of Examples 15-24, and wherein: to generate comprises generating one or more blocks in the blockchain that link adverse event data representing one or more of a recall or a field action event regarding the individual medical device with the unique identifier for the individual medical device.

Example 26 includes the subject matter of Examples 15-25, and further comprising one or more instructions to generate an alert responsive to one or more blocks in the blockchain that includes link adverse event data.

Example 27 includes the subject matter of Examples 15-26, and further comprising one or more instructions to selectively provide access to one or more users to the one or more blocks in the blockchain.

Example 28 includes the subject matter of Examples 15-27, and further comprising one or more instructions to present one or more blocks in the blockchain as a function of the unique identifier for the individual medical device.

Example 29 includes a method comprising: receiving tracking data from a plurality of tracking sources along a medical device lifecycle; and generating one or more blocks in a blockchain to capture the tracking data from the plurality of tracking sources along the medical device lifecycle in one or more distributed ledgers.

Example 30 includes the subject matter of Example 29, and further comprising automatically generating one or more blocks in the blockchain responsive to receiving tracking data from one or more of the plurality of tracking sources along the medical device lifecycle.

Example 31 includes the subject matter of Examples 29-30, and wherein: to automatically generate one or more blocks in the blockchain comprises generating the one or more blocks as a function of a respective tracking source of the plurality of tracking sources.

Example 32 includes the subject matter of Examples 29-31, and wherein: the one or more automated routines are triggered responsive to receiving tracking data from one or more of the plurality of tracking sources along the medical device lifecycle.

Example 33 includes the subject matter of Examples 29-32, and wherein: to generate comprises generating the one or more blocks in the blockchain that include a unique identifying that uniquely identifies an individual medical device.

Example 34 includes the subject matter of Examples 29-33, and wherein: the plurality of tracking sources comprises tracking data representing one or more of design, manufacturing, and supply chain events regarding the individual medical device.

Example 35 includes the subject matter of Examples 29-34, and wherein: generating comprises generating one or more blocks in the blockchain that link tracking data representing one or more of design, manufacturing, and supply chain events regarding the individual medical device with the unique identifier for the individual medical device.

Example 36 includes the subject matter of Examples 29-35, and wherein: generating comprises generating one or more blocks in the blockchain that link tracking data representing healthcare usage events regarding the individual medical device with a unique identifier for the individual medical device.

Example 37 includes the subject matter of Examples 29-36, and wherein: generating comprises generating one or more blocks in the blockchain that link tracking data representing one or more of reprocessing or sterility cycle information regarding the individual medical device with the unique identifier for the individual medical device.

Example 38 includes the subject matter of Examples 29-37, and further comprising enrolling the individual medical device in a clinical study, wherein to generate comprises generating one or more blocks in the blockchain that link tracking data representing one or more of reprocessing or sterility cycle information regarding the individual medical device with the unique identifier for the clinical study.

Example 39 includes the subject matter of Examples 29-38, and wherein: to generate comprises generating one or more blocks in the blockchain that link adverse event data representing one or more of a recall or a field action event regarding the individual medical device with the unique identifier for the individual medical device.

Example 40 includes the subject matter of Examples 29-39, and further comprising generating an alert responsive to one or more blocks in the blockchain that includes link adverse event data.

Example 41 includes the subject matter of Examples 29-40, and further comprising selectively providing access to one or more users to the one or more blocks in the blockchain.

Example 42 includes the subject matter of Examples 29-41, and further comprising presenting one or more blocks in the blockchain as a function of the unique identifier for the individual medical device.

The invention claimed is:

1. A computing system to facilitate integration and tracking of a medical device lifecycle, the computing system comprising:
 a cloud-based server including an application programming interface (API) framework to track a medical device lifecycle for a plurality of medical devices, wherein the API framework is configured to receive calls from a plurality of disparate computing devices associated with the plurality of medical devices along the device lifecycle, wherein the plurality of disparate computing devices make calls to the API framework in response to events occurring during the medical device lifecycle to provide event data comprising design data, manufacturing data, supply chain data, usage data, sales data, and post-market data regarding the plurality of medical devices based on a unique identifier for each of the plurality of medical devices;
 one or more distributed ledgers implemented on the computing system to establish a blockchain that secures the event data relating to the medical device lifecycle regarding the plurality of medical devices received via the API framework;
 wherein the cloud-based server includes a plurality of instructions that, when executed, cause the cloud-based server to:
  receive event data from the plurality of disparate computing devices along the medical device lifecycle regarding the plurality of medical devices received via the API framework, wherein event data received via the API framework comprises manufacturing data, supply chain data, sales data, post-market data, and usage data regarding the plurality of medical devices based on the unique identifier for each of the plurality of medical devices; and
  generate one or more blocks in the blockchain to capture the event data from the plurality of disparate computing devices along the medical device lifecycle in the one or more distributed ledgers in response to receiving event data via the API framework, wherein each block in the blockchain includes the unique identifier for the medical device to which the event data relates;
 wherein one or more blocks in the blockchain link the unique identifier for the medical device with event data to which the medical device relates representing: (i) design, manufacturing, or supply chain events regarding the medical device, (ii) healthcare usage events regarding the medical device, and (iii) reprocessing or sterility cycle information regarding the medical device.

2. The computing system of claim 1, further comprising one or more instructions to generate one or more blocks in the blockchain responsive to receiving tracking data from one or more of the plurality of tracking sources along the medical device lifecycle.

3. The computing system of claim 2, wherein to generate one or more blocks in the blockchain comprises triggering generating the one or more blocks responsive to receiving tracking data from one or more of the plurality of tracking sources along the medical device lifecycle.

4. The computing system of claim 1, wherein the plurality of tracking sources comprises tracking data representing one or more of design, manufacturing, or supply chain events regarding an individual medical device.

5. The computing system of claim 4, wherein the individual medical device comprises one or more of an embedded medical device or a pharmaceutical product.

6. The computing system of claim 4, further comprising one or more instructions to enroll the individual medical device in a clinical study, wherein to generate comprises generating one or more blocks in the blockchain that link tracking data representing one or more of reprocessing or sterility cycle information regarding the individual medical device with the unique identifier for the clinical study.

7. The computing system of claim 4, wherein to generate comprises generating one or more blocks in the blockchain that link adverse event data representing one or more of a recall or a field action event regarding the individual medical device with the unique identifier for the individual medical device.

8. The computing system of claim 7, further comprising one or more instructions to generate an alert responsive to one or more blocks in the blockchain including adverse event data.

9. The computing system of claim 4, further comprising selectively providing access to one or more users to the one or more blocks in the blockchain with an interface that presents one or more blocks in the blockchain as a function of the unique identifier for the individual medical device.

10. A non-transitory computer-readable medium that stores computer executable instructions for causing one or more processors of a server to facilitate integration and tracking of a medical device lifecycle comprising:
 receive event data from a plurality of disparate computing devices associated with the plurality of medical devices along a medical device lifecycle regarding a plurality of medical devices, wherein the event data is received via an API framework for tracking a medical device lifecycle for a plurality of medical devices, wherein the API framework is configured to receive calls from the plurality of disparate computing devices along the device lifecycle, wherein the plurality of disparate computing devices make calls to the API framework in response to events occurring during the medical device lifecycle to provide event data comprising design data, manufacturing data, supply chain data, usage data, sales data, and post-market data regarding the plurality of medical devices based on a unique identifier for each of the plurality of medical devices, wherein event data received via the API framework comprises manufacturing data, supply chain data sales data, post-market data, and usage data regarding the plurality of medical devices based on the unique identifier for each of the plurality of medical devices; and
 generate one or more blocks in a blockchain to capture the event data from the plurality of disparate computing devices along the medical device lifecycle in one or more distributed ledgers in response to receiving event data via the API framework, wherein each block in the blockchain includes the unique identifier for the medical device to which the event data relates;
 wherein one or more blocks in the blockchain link the unique identifier for the medical device with event data to which the medical device relates representing: (i) design, manufacturing, or supply chain events regarding the medical device, (ii) healthcare usage events regarding the medical device, and (iii) reprocessing or sterility cycle information regarding the medical device.

11. The non-transitory computer-readable medium of claim 10, further comprising one or more automated routines to automate generation of one or more blocks in the blockchain responsive to receiving tracking data from one or more of the plurality of tracking sources along the medical device lifecycle.

12. The non-transitory computer-readable medium of claim 11, wherein the one or more automated routines are to generate one or more blocks in the blockchain as a function of a respective tracking source of the plurality of tracking sources in response to receiving tracking data from one or more of the plurality of tracking sources along the medical device lifecycle.

13. The non-transitory computer-readable medium of claim 10, wherein to generate comprises generating the one or more blocks in the blockchain that uniquely identify an individual medical device.

14. The non-transitory computer-readable medium of claim 13, wherein the plurality of tracking sources comprises tracking data representing one or more of design, manufacturing, and supply chain events regarding the individual medical device.

15. The non-transitory computer-readable medium of claim 10, further comprising one or more instructions to enroll the individual medical device in a clinical study, wherein to generate comprises generating one or more blocks in the blockchain that link tracking data representing one or more of reprocessing or sterility cycle information regarding the individual medical device with the unique identifier for the clinical study.

16. The non-transitory computer-readable medium of claim 15, wherein to generate comprises generating one or more blocks in the blockchain that link adverse event data representing one or more of a recall or a field action event regarding the individual medical device with the unique identifier for the individual medical device.

17. The non-transitory computer-readable medium of claim 16, further comprising one or more instructions to generate an alert responsive to one or more blocks in the blockchain that includes adverse event data.

18. The non-transitory computer-readable medium of claim 16, further comprising one or more instructions to selectively provide access to one or more users to the one or more blocks in the blockchain with an interface that presents one or more blocks in the blockchain as a function of the unique identifier for the individual medical device.

19. A method of facilitating integration and tracking of a medical device lifecycle, the method comprising:
receiving event data regarding an individual medical device from a manufacturing plant associated with the individual medical device via an application programming interface (API) framework on a cloud-based server, wherein the event data received from the manufacturing plant comprises one or more manufacturing records that identify the individual medical device with an unique device identifier;
capturing the one or more manufacturing records regarding the individual medical device by generating one or more blocks of a blockchain as a function of the unique device identifier associated with the individual medical device;
receiving event data regarding the individual medical device from a supply chain entity associated with the individual medical device via an application programming interface (API) framework on a cloud-based server, wherein the event data received from the supply chain entity comprises one or more transportation and delivery records that identify the individual medical device with the unique device identifier;
capturing the one or more transportation and delivery records regarding the individual medical device by generating one or more blocks of the blockchain as a function of the unique device identifier associated with the individual medical device;
receiving event data regarding the individual medical device from a retailer entity associated with the individual medical device via an application programming interface (API) framework on a cloud-based server, wherein the event data received from the retailer entity comprises one or more sales records that identify the individual medical device with the unique device identifier;
capturing the one or more sales records regarding the individual medical device by generating one or more blocks of the blockchain as a function of the unique device identifier associated with the individual medical device;
receiving event data regarding the individual medical device from a patient in whom the individual medical device is installed via an application programming interface (API) framework on a cloud-based server, wherein the event data received from the patient comprises one or more usage records that identify the individual medical device with the unique device identifier;
capturing the one or more usage records regarding the individual medical device by generating one or more blocks of the blockchain as a function of the unique device identifier associated with the individual medical device, wherein one or more blocks in the blockchain link the unique identifier for the medical device with event data to which the individual medical device relates representing: (i) design, manufacturing, or supply chain events regarding the medical device, (ii) healthcare usage events regarding the medical device, and (iii) reprocessing or sterility cycle information regarding the medical device;
receiving a query from a user interface that includes the unique device identifier associated with the individual medical device; and
in response to the query, displaying in the user interface each block from the blockchain that contains the unique device identifier associated with the individual medical device.

* * * * *